US009034277B2

(12) United States Patent
Gu et al.

(10) Patent No.: US 9,034,277 B2
(45) Date of Patent: May 19, 2015

(54) SURFACE PREPARATION FOR A MICROFLUIDIC CHANNEL

(75) Inventors: Alex Gu, Plymouth, MN (US); Mark Washa, Plymouth, MN (US)

(73) Assignee: Honeywell International Inc., Morristown, NJ (US)

( * ) Notice: Subject to any disclaimer, the term of this patent is extended or adjusted under 35 U.S.C. 154(b) by 1083 days.

(21) Appl. No.: 12/603,477

(22) Filed: Oct. 21, 2009

(65) Prior Publication Data

US 2010/0104479 A1 Apr. 29, 2010

Related U.S. Application Data

(60) Provisional application No. 61/108,405, filed on Oct. 24, 2008.

(51) Int. Cl.

*G01N 33/52* (2006.01)
*B01L 3/00* (2006.01)
*B24B 1/00* (2006.01)
*B29C 59/00* (2006.01)

(52) U.S. Cl.

CPC ....... *B01L 3/502707* (2013.01); *B01L 2300/16* (2013.01); *B01L 2400/086* (2013.01)

(58) Field of Classification Search

USPC .................. 422/400–404, 500–507; 264/293; 216/94, 83; 427/307
See application file for complete search history.

(56) References Cited

U.S. PATENT DOCUMENTS

| | | | | |
|---|---|---|---|---|
| 5,424,219 | A * | 6/1995 | Jirikowski | 436/518 |
| 6,167,948 | B1 * | 1/2001 | Thomas | 165/104.26 |
| 6,382,228 | B1 | 5/2002 | Cabuz et al. | |
| 6,549,275 | B1 | 4/2003 | Cabuz et al. | |
| 6,594,009 | B2 | 7/2003 | Saccomanno | |
| 6,597,438 | B1 | 7/2003 | Cabuz et al. | |
| 6,700,130 | B2 | 3/2004 | Fritz | |
| 6,911,894 | B2 | 6/2005 | Bonne | |
| 6,970,245 | B2 | 11/2005 | Fritz et al. | |
| 7,000,330 | B2 | 2/2006 | Schwichtenberg et al. | |
| 7,016,022 | B2 | 3/2006 | Fritz et al. | |
| 7,061,595 | B2 | 6/2006 | Cabuz et al. | |
| 7,130,046 | B2 | 10/2006 | Fritz et al. | |
| 7,168,675 | B2 | 1/2007 | Cabuz et al. | |
| 7,215,425 | B2 | 5/2007 | Rezachek et al. | |
| 7,258,003 | B2 | 8/2007 | Padmanabhan et al. | |
| 7,262,838 | B2 | 8/2007 | Fritz | |
| 7,277,166 | B2 | 10/2007 | Padmanabhan et al. | |
| 7,283,223 | B2 | 10/2007 | Fritz | |
| 7,312,870 | B2 | 12/2007 | Fritz et al. | |

(Continued)

FOREIGN PATENT DOCUMENTS

| | | |
|---|---|---|
| WO | 9935497 | 7/1999 |
| WO | 2006110177 | 10/2006 |

(Continued)

*Primary Examiner* — Jill Warden
*Assistant Examiner* — Timothy G Kingan
(74) *Attorney, Agent, or Firm* — Seager, Tufte & Wickhem LLC

(57) ABSTRACT

A microfluidic cartridge having a microfluidic channel may have at least one surface that has been roughened, etched or otherwise treated to alter its surface characteristics. In some instances, a microfluidic cartridge may have a microfluidic channel that is configured to provide even distribution of a lysing reagent across the channel. The surface may be roughened or etched using a laser, an abrasive, application of a solvent or in any other suitable manner.

16 Claims, 6 Drawing Sheets

(56) References Cited

U.S. PATENT DOCUMENTS

| | | | | |
|---|---|---|---|---|
| 7,333,197 | B2 | 2/2008 | Fritz et al. | |
| 7,420,659 | B1 | 9/2008 | Cabuz | |
| 7,445,017 | B2 | 11/2008 | Cabuz et al. | |
| 7,471,394 | B2 | 12/2008 | Padmanabhan | |
| 7,485,153 | B2 | 2/2009 | Padmanabhan et al. | |
| 7,486,387 | B2 | 2/2009 | Fritz | |
| 7,497,997 | B2 | 3/2009 | Glezer et al. | |
| 7,551,278 | B2 | 6/2009 | Cole | |
| 2002/0072110 | A1 * | 6/2002 | Lienau et al. | 435/270 |
| 2004/0213963 | A1 * | 10/2004 | Bourdelais et al. | 428/188 |
| 2004/0259162 | A1 * | 12/2004 | Kappel et al. | 435/7.1 |
| 2006/0115623 | A1 | 6/2006 | Aizenberg et al. | |
| 2006/0160209 | A1 * | 7/2006 | Larson et al. | 435/287.2 |
| 2006/0278287 | A1 | 12/2006 | Fielden et al. | |
| 2007/0009709 | A1 * | 1/2007 | Krishnan et al. | 428/141 |
| 2007/0140913 | A1 | 6/2007 | Cohen et al. | |
| 2007/0219366 | A1 * | 9/2007 | Gumbrecht et al. | 536/25.4 |
| 2008/0296260 | A1 | 12/2008 | Tserepi et al. | |
| 2009/0130658 | A1 * | 5/2009 | Barlag et al. | 435/6 |

FOREIGN PATENT DOCUMENTS

| | | |
|---|---|---|
| WO | 2007075287 | 7/2007 |
| WO | 2007091097 | 8/2007 |
| WO | 2008035045 | 3/2008 |
| WO | 2008114063 | 9/2008 |

* cited by examiner

SURFACE PREPARATION FOR A MICROFLUIDIC CHANNEL

This application claims the benefit of U.S. Provisional Patent Application No. 61/108,405, filed Oct. 24, 2008, which is hereby incorporated by reference.

TECHNICAL FIELD

The present disclosure relates generally to microfluidic cartridges having one or more microfluidic channels, and more particularly to microfluidic channels that have an applied coating on an inner surface.

BACKGROUND

There has been a growing interest in the manufacture and use of microfluidic systems for the acquisition of chemical and biological information. Microfluidic systems often have a microfluidic cartridge that is capable of performing various microfluidic functions and/or analysis. For example, a microfluidic cartridge may be adapted to help perform sample analysis and/or sample manipulation functions, such as chemical, biological and/or physical analyses and/or manipulation functions. Microfluidic systems can have the advantage of, for example, shorter response time, smaller required sample volumes, lower reagent consumption, and in some cases, the capability to perform such analysis in the field. When hazardous materials are used or generated, performing reactions in microfluidic volumes may also enhance safety and reduces disposal quantities.

In some cases, a microfluidic cartridge is used in conjunction with a cartridge reader instrument. The cartridge reader instrument may, for example, provide support functions to the microfluidic cartridge. For example, and in some cases, a cartridge reader may provide electrical control signals, light beams and/or light detectors, pneumatic control flows, electric and/or magnetic flow drive fields, signal processing, and/or other support functions.

SUMMARY

The present disclosure relates generally to microfluidic cartridges having one or more microfluidic channels, and more particularly to microfluidic channels having one or more inner surfaces that have been treated to alter the surface characteristics of the one or more inner surfaces. In some cases, a coating may then be applied to one or more of the inner surfaces, but this is not required.

In some cases, the surface treatment may roughen, etch and/or otherwise alter the surface texture of the inner surface, and may be accomplished through the use of, for example, a laser, an abrasive and/or the application of a solvent. In some instances, such a surface treatment may provide for improved flow characteristics within the channel by encouraging a desired flow pattern. In some cases, the surface treatment may result in a more even distribution of the coating across the microfluidic channel. It is contemplated that the coating may be any suitable coating such as a lysing reagent, a sphering reagent, a stain, a hydrophobic coating, a hydrophilic coating, or any other suitable coating for the desired application.

The above summary is not intended to describe each disclosed embodiment or every implementation of the disclosure. The Description which follows more particularly exemplify these embodiments.

BRIEF DESCRIPTION OF THE FIGURES

The following description should be read with reference to the drawings. The drawings, which are not necessarily to scale, depict selected embodiments and are not intended to limit the scope of the disclosure. The disclosure may be more completely understood in consideration of the following detailed description of various embodiments in connection with the accompanying drawings, in which.

Figure 1:
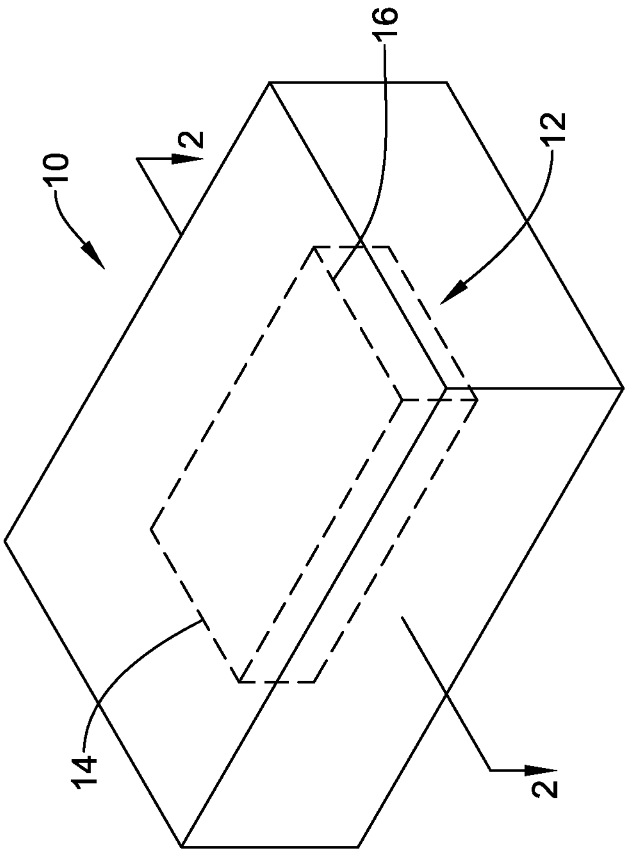
FIG. 1 is a schematic view of an illustrative but non-limiting microfluidic cartridge.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DESCRIPTION

The following description should be read with reference to the drawings, in which like elements in different drawings are numbered in like fashion. The drawings, which are not necessarily to scale, depict selected embodiments and are not intended to limit the scope of the invention. Although examples of construction, dimensions, and materials are illustrated for the various elements, those skilled in the art will recognize that many of the examples provided have suitable alternatives that may be utilized.

FIG. 1 is a schematic top view of an illustrative microfluidic cartridge. It should be understood that the microfluidic cartridge shown generally at 10 is only illustrative, and that the disclosure pertains to any microfluidic cartridge regardless of form, function or configuration. For example, the microfluidic cartridge may be used for hematology, flow cytometry, clinical chemistry, electrolyte measurements, etc. It is also contemplated that the illustrative microfluidic cartridge 10 may be made from any suitable material or material system including, for example, glass, silicon, one or more polymers, or any other suitable material or material system, or combination of materials or material systems. At least some of microfluidic cartridge 10 may be formed of an acrylic material, but this is not required.

In some instances, microfluidic cartridge 10 may include a microfluidic channel 12. While a single microfluidic channel is illustrated, it will be appreciated that microfluidic cartridge 10 may include two or more microfluidic channels, reservoirs, and/or other structures as appropriate. As illustrated, microfluidic channel 12 extends from a first location 14 within microfluidic cartridge 10 to a second location 16 within microfluidic cartridge 10. It will be appreciated that microfluidic channel 12 is intended to generically represent a variety of possible internal fluid passageways and the like that may be included in microfluidic cartridge 10. In some cases, the microfluidic channel 12 may extend out the side of the microfluidic cartridge 10 to, for example, receive a sample, a reagent or other fluid, depending on the application.

Microfluidic channel 12 may be formed in any suitable manner. In some cases, microfluidic cartridge 10 is formed by sandwiching together (e.g. laminating) a number of distinct layers. For example, microfluidic channel 12 may be formed via an elongate aperture formed within a particular layer(s). The top and bottom of microfluidic channel 12 may be formed by the layers immediately above and below the particular layer(s) including the elongate aperture. In this, reference to up and down are relative and refer only to the illustrated orientation. In some cases, at least some of the layers forming microfluidic cartridge 10 may be polymeric, but this is not required in all embodiments.

Figure 2:
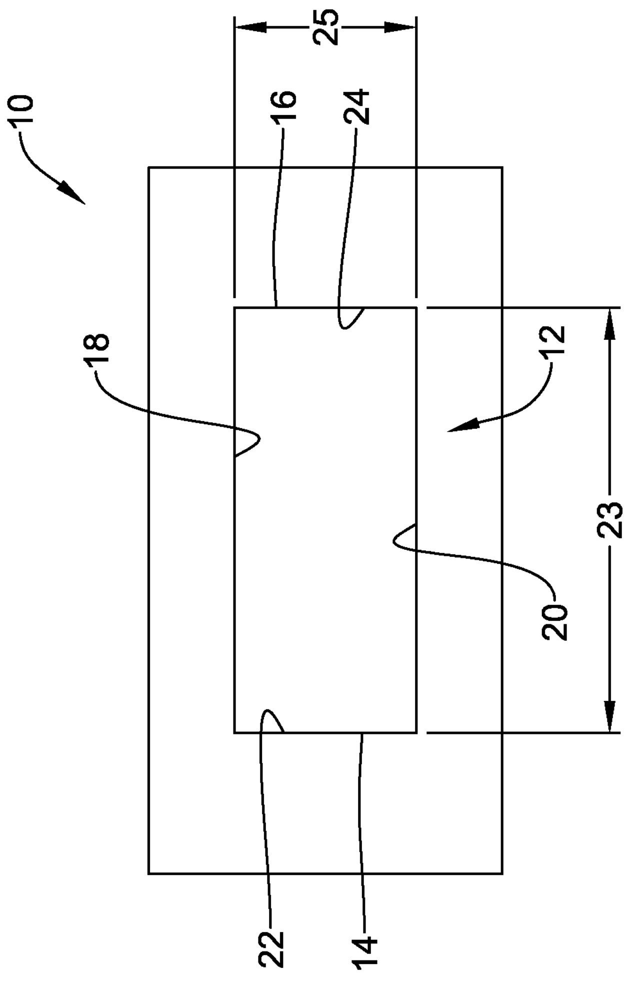
FIG. 2 is a cross-sectional view of the microfluidic cartridge of FIG. 1.

FIG. 2 is a cross-sectional view of the illustrative microfluidic cartridge 10, taken along line 2-2 of FIG. 1. Microfluidic channel 12 may be seen, in the illustrated orientation, as having four channel walls 18, 20, 22, and 24. As shown, these channel walls may include a bottom channel wall 20, a top channel wall 18, a first side channel wall 22 and a second side channel wall 24. In some cases, microfluidic channel 12 may be considered as having a width 23 that is in the range of several millimeters to several tens of millimeters and a height 25 that is in the range of about 1 to about 50 or 100 or even 250 micrometers, but these dimensions are only illustrative. It will be appreciated that microfluidic channel 12 may have a first end corresponding to first location 14 and a second end corresponding to second location 16, although in some cases microfluidic channel 12 may start or stop adjacent to other internal structures such as reservoirs, valves, pumps and the like, or may extend out the side of the microfluidic cartridge 10 to, for example, receive a sample, a reagent or other fluid, depending on the application.

In some cases, a microfluidic channel 12 may be used to pass various fluids such as reagents and/or a sample of interest. In some instances, it may be useful to encourage a desired flow pattern, such as turbulent flow through the microfluidic channel 12. For example, in some cases, turbulent flow may encourage mixing within the flowing fluid. In some cases, mixing may be beneficial for whatever analysis is being performed on the flowing fluid. It will be recognized that turbulent flow may provide mixing advantages that are not necessarily provided by laminar flow.

In some cases, a coating may be applied on one or more of the channel walls 18, 20, 22, and/or 24 of microfluidic channel 12 to help support the analysis of the microfluidic cartridge 10. For example, when microfluidic cartridge 10 is a blood analysis cartridge, a reagent may be deposited or otherwise provided on one or more of the channel walls 18, 20, 22, and/or 24 to interact with a blood sample as the blood sample is passed through the microfluidic channel 12. However, when such a reagent is deposited or otherwise provided on one or more of the channel walls 18, 20, 22, and/or 24, the reagent may be preferentially deposited on only certain parts of the microfluidic channel 12, such as near or on certain side walls such as side walls 22 and 24. Also, and in some cases, fluid flowing through a microfluidic channel 12 may have uneven exposure to any functional coating that may be disposed on the channel wall, with higher fluid flow rates near the center of a microfluidic channel 12 than near certain side walls such as side walls 22 and 24. One or both of these effects can cause uneven fluid characteristics such as lower reagent concentration in certain parts of the flow stream, which can result in uneven or otherwise less than desirable results.

Figure 3:
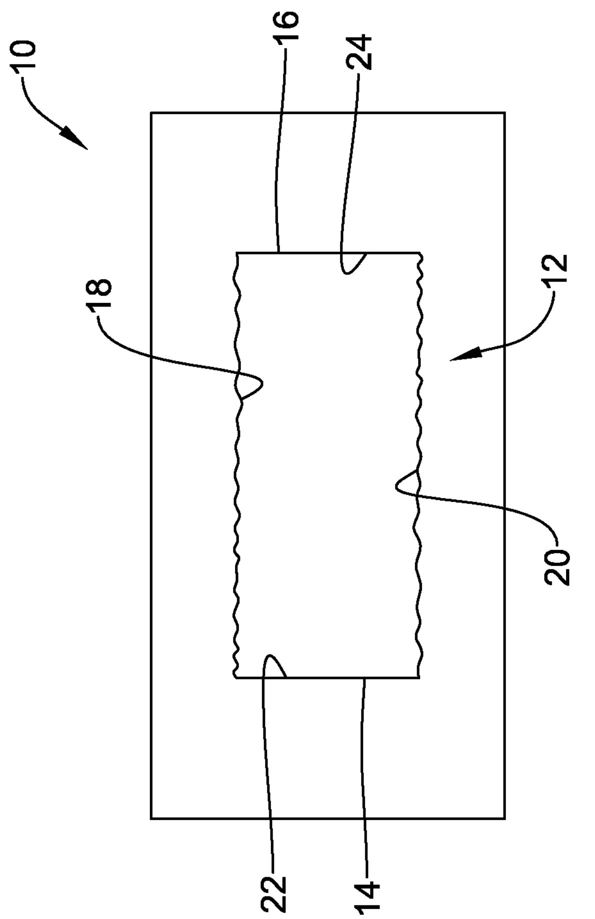
FIG. 3 is a more detailed cross-sectional view of the microfluidic cartridge of FIG. 1 showing treated upper and lower surfaces.

To enhance the performance characteristics of the resulting coating, at least part of one or more of the channel walls 18, 20, 22, and/or 24 may be first treated to alter the surface characteristics, as shown in FIG. 3. Then, once the surface(s) is treated, a desired coating may be applied to the treated surface. In some cases, the surface treatment may roughen, etch and/or otherwise alter the surface texture of the one or more of the channel walls 18, 20, 22, and/or 24, and may be accomplished through the use of, for example, a laser, an abrasive and/or the application of a solvent. In some instances, such a surface treatment may result in a more even distribution of the coating across the one or more of the channel walls 18, 20, 22, and/or 24 of the microfluidic channel 12. It is contemplated that the coating may be any suitable coating such as a functional reagent, a lysing reagent, a sphering reagent, a stain, a hydrophobic coating, a hydrophilic coating, or any other suitable coating for the desired application.

In some instances, the treated surface may provide for increased surface area for subsequent application of the coating, and thus may permit retention of a relatively greater amount of the coating. In some cases, the treated surface may result in better adhesion of the coating and/or may permit a more even deposition and/or retention of the coating.

In some cases, the surface(s) may be treated before or while cartridge 10 is assembled, but this is not required. It is contemplated that the surface(s) may be treated in a variety of ways. For example, in some instances, the surface(s) may be etched by making several laser passes over the surface. It will be appreciated that relative power level of the laser may vary, depending on the substrate being etched as well as the particular laser being used. In one illustrative example, the surface(s) may be laser etched using a 630-680 nanometer, 5 mw laser from Universal Laser Systems of Scottsdale, Ariz. For example, the laser may be used with a power setting of about 27 percent and a speed setting of about 95 percent with an acrylic and/or ACA (adhesive carrier adhesive) substrate. In some cases, laser etching may provide a relatively uniform pattern such as parallel grooves formed within the etched surface. The parallel grooves may, for example, extend lengthwise along the treated surface, but this is not required as the grooves may instead be disposed at an acute angle with respect to a longitudinal axis.

Another illustrative method of treating one or more of the channel walls 18, 20, 22, and/or 24 includes applying a solvent to the surface(s). In an illustrative example, acetone may be used if the surface(s) is formed of or otherwise includes an acrylic or similar material. The acetone may be applied to one or more of the channel walls 18, 20, 22, and/or 24 and then be allowed to dry. The acetone may dissolve portions of the acrylic, leaving small pits in the resulting surface, thereby forming a roughened surface. In some cases, the roughened surface may have a random appearance.

It will be appreciated that other solvents may be used, depending on the particular material used to form the one or more of the channel walls 18, 20, 22, and/or 24. Another illustrative method of treating one or more of the channel walls 18, 20, 22, and/or 24 includes a mechanical abrasion process. For example, the one or more of the channel walls 18, 20, 22, and/or 24 may be treated with an abrasive material such as sandpaper, grinding, and/or sandblasting. After one or more of the channel walls 18, 20, 22, and/or 24 has been treated, an appropriate coating may be applied to the treated surface.

In some cases, the coating may be a cell lysing reagent. It will be appreciated that one or more additional surfaces within microfluidic channel 12 may be coated with the cell lysing reagent. A variety of cell lysing reagents may be used. For example, and in some cases, any surfactant that may adhere to the treated surface and can sufficiently disrupt cell walls may be used. In some cases, an appropriate surfactant may be a surfactant that can dissolve lipids.

In some instances, the cell lysing reagent may be a salt or a salt mixture that can be applied to the treated surface(s), followed by a drying step. In some cases, the salt solution may be printed onto the treated surface(s). An illustrative example of a suitable salt is sodium deoxycholate, which may be used by itself or in a mixture with other salts, if desired.

EXAMPLES

Figure 4:
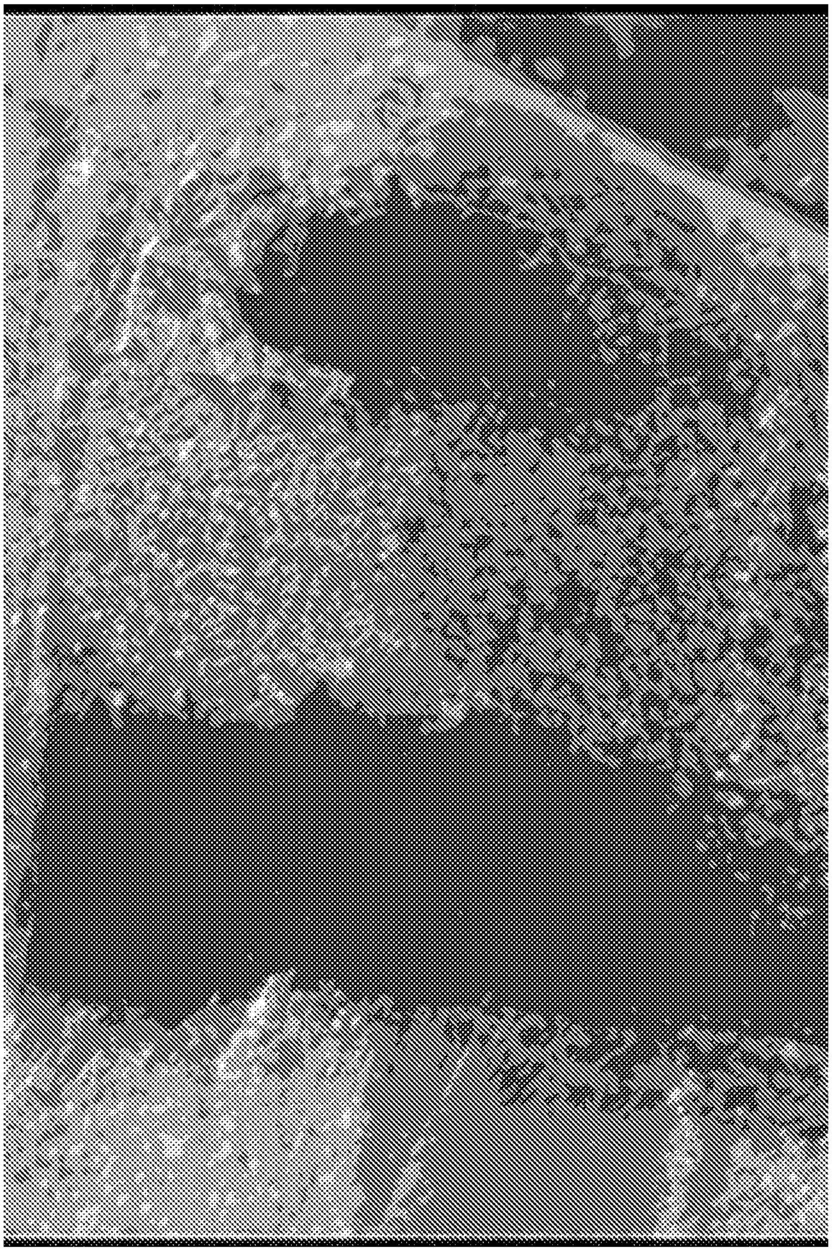
FIG. 4 is a picture of a channel with an uneven lysing reagent distribution.

FIG. 4 provides a comparative example, showing a microfluidic cartridge channel that has not been surface-treated, and exhibits uneven distribution of the cell lysing reagent. As can be seen in FIG. 4, untreated surfaces lack sufficient structure for the cell lysing reagent (sodium deoxychlolate) to adhere to as it dries. As the salt dries, the lack of adhesion results in a similar phenomenon as beading up of water on a windshield. As a result, the salt groups up in a non-uniform manner on the surface. This results in an uneven salt distribution, which lyses a sample flowing through the microfluidic channel unevenly and with less than desirable results. The blank areas where there is no salt may allow a pathway of least resistance, which can allow a blood sample passing through the channel to bypass at least some of the lysing reagent.

Figure 5:
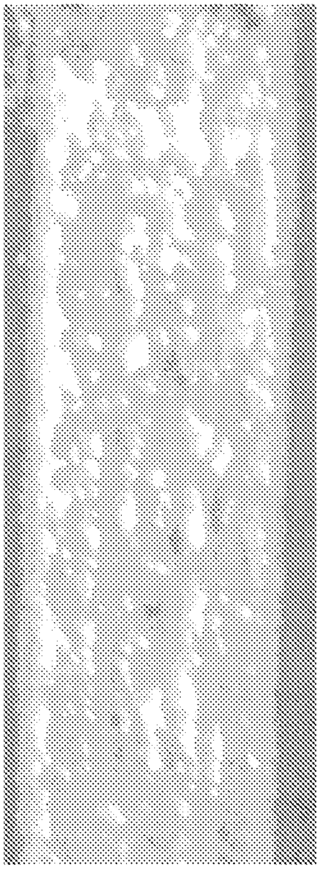
FIG. 5 is a picture of an illustrative channel with an even lysing reagent distribution.

FIG. 5 provides an example where the surface has been treated before applying the lysing reagent. In this example, an acrylic capping layer was etched using a laser. The illustrative capping layer would be used to form a top surface of a microfluidic channel. The laser power was adjusted so as to roughen the acrylic surface of the capping layer to facilitate the adhering of the salt solution without excessively cutting into the surface. The laser power was controlled during the laser etching sequence, as too much power would cut through and/or make fissures that will be too deep, and may even leave areas that might allow bubbles to form within the channel. Too little power may not have the desired surface effect, leading to poor salt adhesion. The surface shown in FIG. 5 was etched using a 630-680 nanometer, 5 mw laser from Universal Laser Systems of Scottsdale, Ariz. The settings were approximately 27% power and 95% speed. This treatment etched the surface without over cutting or over heating. A sodium deoxycholate salt solution was then printed onto the etched surface and allowed to dry. A uniform salt distribution was obtained, as seen in FIG. 5. Uniform printing of the lysing reagent can result in uniform sample lysing, uniform specimen coloration, and increased precision in coloric measurements.

Figure 6:
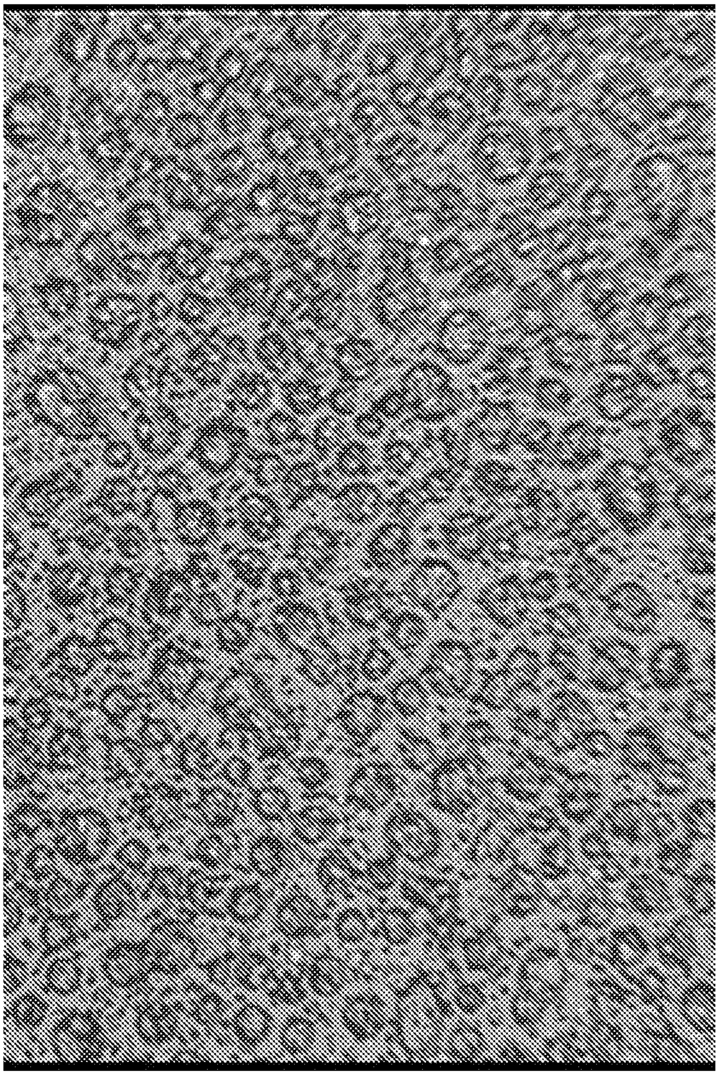
FIG. 6 is a picture of an illustrative channel having surface modification.

FIG. 6 illustrates another surface treatment process. In this process, acetone was used to etch the surface. Acetone was added to the acrylic surface and was allowed to dry. The acrylic, which is initially very smooth, is roughened as the acetone dissolves areas of the acrylic, attacks it, and leaves behind tiny pits as it dries. A sodium deoxycholate salt solution was applied and then allowed to dry. FIG. 6 reveals that the roughened, salted surface resembles thousands of ball bearings at 50× magnification. The resulting roughened surface provides improved surface area and salt retention.

The disclosure should not be considered limited to the particular examples described above, but rather should be understood to cover all aspects of the invention as set out in the attached claims. Various modifications, equivalent processes, as well as numerous structures to which the invention can be applicable will be readily apparent to those of skill in the art upon review of the instant specification.

We claim:

1. A microfluidic cartridge comprising:

a channel for transporting a fluid from a first location in the microfluidic cartridge to a second location in the microfluidic cartridge, the channel comprising a bottom channel wall, a top channel wall, a first side channel wall and a second side channel wall;

wherein the top channel wall and the bottom channel wall are rougher than the first side channel wall and the second side channel wall; and wherein a functional reagent is deposited on the rougher top and bottom channel walls.

2. The microfluidic cartridge of claim 1, wherein the functional reagent comprises a lysing reagent.

3. The microfluidic cartridge of claim 2, wherein the lysing reagent comprises a salt.

4. The microfluidic cartridge of claim 2, wherein the lysing reagent comprises sodium deoxycholate.

5. A method of making a microfluidic cartridge for processing a biological sample, comprising:

roughening a surface of a first cartridge layer;

roughening a surface of a second cartridge layer;

applying a functional reagent to the roughened surface of the first cartridge layer;

applying a functional reagent to the roughened surface of the second cartridge layer;

laminating the first cartridge layer and the second cartridge layer with an intermediate cartridge layer therebetween, wherein the intermediate cartridge layer comprises an elongated aperture that, together with the roughened surface of the first cartridge layer and the roughened surface of the second cartridge layer, defines a microfluidic channel for processing the biological sample.

6. The method of claim 5, wherein applying the functional reagent to the roughened surface of the first cartridge layer comprises printing a cell lysing reagent onto the roughened surface of the first cartridge layer.

7. The method of claim 5, wherein applying the functional reagent to the roughened surface of the first cartridge layer comprises applying a solution comprising sodium deoxychlorate to the roughened surface of the first cartridge layer, followed by a drying step.

8. The method of claim 5, wherein roughening the surface of the first cartridge layer comprises laser etching.

9. The method of claim 5, wherein roughening the surface of the first cartridge layer comprises making multiple passes with a laser to etch the surface.

10. The method of claim 5, wherein roughening the surface of the first cartridge layer comprises applying a solvent to the surface.

11. The microfluidic cartridge of claim 10, wherein roughening the surface of the first cartridge layer comprises applying acetone to the surface.

12. The method of claim 5, wherein roughening the surface of the first cartridge layer comprises using an abrasive.

13. A microfluidic cartridge comprising:

a polymeric substrate;

a microfluidic channel formed within the substrate, the microfluidic channel comprising a bottom channel wall, a top channel wall, a first side channel wall and a second side channel wall, wherein the top channel wall and the bottom channel wall are rougher than the first side channel wall and the second side channel wall; and a functional reagent applied to the rougher top and bottom channel walls but not the first side channel wall and the second side channel wall.

14. The microfluidic cartridge of claim 13, wherein the functional reagent is relatively evenly distributed across the rougher top and bottom channel walls.

15. The microfluidic cartridge of claim 13, wherein the functional reagent comprises one or more salts.

16. The microfluidic cartridge of claim 15, wherein the one or more salts comprises sodium deoxycholate.

* * * * *